(12) United States Patent
Wu (10) Patent No.: US 12,048,421 B2
(45) Date of Patent: Jul. 30, 2024

(54) SALIVA DETECTION DEVICE, SALIVA DETECTION SYSTEM AND OPERATION METHOD THEREOF

(71) Applicant: BOE TECHNOLOGY GROUP CO., LTD., Beijing (CN)

(72) Inventor: Zheng Wu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 1098 days.

(21) Appl. No.: 16/768,270

(22) PCT Filed: Dec. 23, 2019

(86) PCT No.: PCT/CN2019/127557
§ 371 (c)(1),
(2) Date: May 29, 2020

(87) PCT Pub. No.: WO2020/151440
PCT Pub. Date: Jul. 30, 2020

(65) Prior Publication Data
US 2021/0204917 A1 Jul. 8, 2021

(30) Foreign Application Priority Data

Jan. 25, 2019 (CN) .......................... 201910074709.9

(51) Int. Cl.
*A61B 10/00* (2006.01)
*A61B 5/145* (2006.01)
(Continued)

(52) U.S. Cl.
CPC ...... *A61B 10/0051* (2013.01); *A61B 5/14532* (2013.01); *A61B 5/1486* (2013.01);
(Continued)

(58) Field of Classification Search
CPC ............ A61B 10/0051; A61B 5/14532; A61B 5/1486; A61B 2560/0214;
(Continued)

(56) References Cited

U.S. PATENT DOCUMENTS

2014/0084748 A1 3/2014 Wang et al.
2016/0338626 A1* 11/2016 Wang ...................... H01M 8/22

FOREIGN PATENT DOCUMENTS

CN 102323310 A 1/2012
CN 202195962 U 4/2012
(Continued)

OTHER PUBLICATIONS

First Office Action dated Feb. 3, 2020 corresponding to Chinese Application No. 201910074709.9.
(Continued)

*Primary Examiner* — Jill A Warden
*Assistant Examiner* — John McGuirk
(74) *Attorney, Agent, or Firm* — Nath, Goldberg & Meyer; Joshua B. Goldberg (57) ABSTRACT

A saliva detection device, a saliva detection system and an operation method of the same are provided. The saliva detection device includes a flexible friction power generation assembly configured to supply power to the saliva detection device and including: a first electrode; a first macromolecule polymer layer which is disposed in contact with a surface of the first electrode and has a concave-convex structure on a surface thereof distal to the first electrode; a second macromolecule polymer layer having a concavo-convex structure on a surface thereof proximal to the first macromolecule polymer layer and a second electrode disposed in contact with a surface of the second macromolecule polymer layer distal to the concavo-convex structure thereof, in response to flexible deformation of the
(Continued)

flexible friction power generation assembly, the concavo-convex structures of the first macromolecule polymer layer and the second macromolecule polymer layer rub against each other.

16 Claims, 4 Drawing Sheets

(51) Int. Cl.
*A61B 5/1486* (2006.01)
*G01N 27/327* (2006.01)
*H02N 1/04* (2006.01)

(52) U.S. Cl.
CPC ............ *G01N 27/3273* (2013.01); *H02N 1/04* (2013.01); *A61B 2560/0214* (2013.01); *A61B 2562/0247* (2013.01); *A61B 2562/029* (2013.01)

(58) Field of Classification Search
CPC ...... A61B 2562/0247; A61B 2562/029; G01N 27/3273; G01N 27/3272; G01N 27/26; H02N 1/04
See application file for complete search history.

(56) References Cited

FOREIGN PATENT DOCUMENTS

| | | | |
|---|---|---|---|
| CN | 202305465 U | * | 7/2012 |
| CN | 202305465 U | | 7/2012 |
| CN | 102684546 A | | 9/2012 |
| CN | 202793842 U | | 3/2013 |
| CN | 103780120 A | * | 5/2014 |
| CN | 103780120 A | | 5/2014 |
| CN | 104660095 A | | 5/2015 |
| CN | 104856662 A | | 8/2015 |
| CN | 204666397 U | | 9/2015 |
| CN | 105973883 A | | 9/2016 |
| CN | 106104264 A | | 11/2016 |
| CN | 205826351 U | | 12/2016 |
| CN | 205826351 U | * | 12/2016 |
| JP | 2015192717 A | * | 11/2015 |
| WO | 2011118758 A1 | | 9/2011 |

OTHER PUBLICATIONS

Second Office Action dated Aug. 20, 2020 corresponding to Chinese Application No. 201910074709.9.

* cited by examiner

SALIVA DETECTION DEVICE, SALIVA DETECTION SYSTEM AND OPERATION METHOD THEREOF

CROSS-REFERENCE TO RELATED APPLICATIONS

This is a National Phase Application filed under 35 U.S.C. 371 as a national stage of PCT/CN2019/127557, filed Dec. 23, 2019, an application claiming the benefit of Chinese Application No. 201910074709.9, filed Jan. 25, 2019, the content of each of which is hereby incorporated by reference in its entirety.

TECHNICAL FIELD

The present disclosure relates to the field of medical instruments, and in particular to a saliva detection device, a saliva detection system and an operation method of the saliva detection system.

BACKGROUND

It is easy to obtain and store saliva, and biomarkers of various diseases exist in the saliva, so that the saliva can be used for early diagnosis and treatment of the diseases for effectively reducing a probability of serious diseases, and the saliva plays an important role in treatment of possibly occurring complications, therefore the saliva, as a continuously regenerating fluid, provides a huge database of "physiological snapshots", which makes using the saliva as a diagnostic sample more practical. Moreover, it is easy and convenient to sample the saliva, which avoids pain and anxiety caused by a traditional invasive sample collection method, such as blood sampling or tissue biopsy, and thus a saliva sample has very important value in clinical chemical examination.

SUMMARY

The present disclosure provides a saliva detection device, a saliva detection system and an operation method thereof.

According to a first aspect of the present disclosure, there is provided a saliva detection device, including a flexible friction power generation assembly configured to supply power to the saliva detection device and, in turn, including: a first electrode; a first macromolecule polymer layer which is disposed in contact with a surface of the first electrode and has a concave-convex structure on a surface thereof distal to the first electrode; a second macromolecule polymer layer having a concavo-convex structure on a surface thereof proximal to the first macromolecule polymer layer; and a second electrode disposed in contact with a surface of the second macromolecule polymer layer distal to the concave-convex structure thereof, and in response to flexible deformation of the flexible friction power generation assembly, the concave-convex structures of the first macromolecule polymer layer and the second macromolecule polymer layer rub against each other, and an electrical signal is output through the first electrode and the second electrode.

In some implementations, the deformation of the flexible friction power generation assembly includes bending, and the flexible friction power generation assembly is configured to output a periodic alternating current electrical signal through the first electrode and the second electrode by repeated bending and recovering.

In some implementations, the saliva detection device further includes: a stepping motor configured to periodically oscillate to drive the flexible friction power generation assembly to repeatedly bend and recover.

In some implementations, the saliva detection device further includes an electrical storage element configured to store electrical energy generated by the flexible friction power generation assembly.

In some implementations, the concavo-convex structure is a micro-scale and/or nano-scale concavo-convex structure.

In some implementations, the first electrode, the first macromolecule polymer layer, the second macromolecule polymer layer and the second electrode of the flexible friction power generation assembly are stacked in a stacking direction perpendicular to an opening direction of the electrochemical reaction sample groove, and a thickness of the flexible friction power generation assembly is consistent with a dimension of a cross section of the sample collector taken along the stacking direction.

In some implementations, the thickness of the friction power generation assembly is about 380 µm.

In some implementations, the sample collector has an overall curvature such that both ends thereof are higher than the middle part in a length direction thereof, and the electrochemical reaction sample groove is provided in the sample collector to collect the saliva sample.

In some implementations, the sample collector is made of a flexible material the same as that of the first macromolecule polymer layer and the second macromolecule polymer layer.

In some implementations, there is a difference in friction electrode sequence between a material of the first macromolecule polymer layer and a material of the second macromolecule polymer layer.

In some implementations, the saliva detection device further comprises a sample collector, an electrochemical sensor and an electric signal transmission member, wherein the sample collector is provided with a curvature, so that a middle part thereof is lower than two ends thereof, and an electrochemical reaction sample groove is arranged in the sample collector; the electrochemical sensor is arranged in the electrochemical reaction sample groove to detect a component in a saliva sample and generate a corresponding electric signal; and the electrical signal transmission member is configured to transmit the electrical signal.

In some implementations, the flexible friction power generation assembly is disposed at a bottom of the sample collector and is wrapped by a flexible waterproof insulating material. In some implementations, the first macromolecule polymer layer and the second macromolecule polymer layer are made of a hydrophobic material.

In some implementations, the saliva detection device further includes: a conductive pillar arranged on the sample collector and configured to electrically stimulate a salivary gland of an examinee wearing the saliva detection device.

In some implementations, an outer wall of the sample collector is provided with a liquid inlet for allowing the saliva sample to enter the electrochemical reaction sample groove.

In some implementations, the saliva detection device further includes: a sample amount reminding member configured to determine an amount of the saliva sample in the electrochemical reaction sample groove, and to issue a reminder and initiate a detection of the electrochemical sensor in response to the detected amount of the saliva sample reaching a preset threshold.

In some implementations, the sample amount reminding member includes any one of the following means provided in the electrochemical reaction sample groove to determine the amount of the saliva sample in the electrochemical reaction sample groove based on a detection result of the means: a humidity sensor configured to detect humidity within the electrochemical reaction sample groove; a liquid level sensor configured to detect a liquid level within the electrochemical reaction sample groove; and a pressure sensor configured to detect a pressure within the electrochemical reaction sample groove.

In some implementations, the electrochemical sensor is configured to detect a content of glucose in the saliva sample and includes a working electrode in a form of nanospheres which are loaded with riboflavin adenine nucleotide complex glucose dehydrogenase or glucose oxidase.

According to a second aspect of the present disclosure, there is provided a saliva detection system including the saliva detection device of the present disclosure and a terminal, the terminal including: a communication interface configured to receive the electrical signal transmitted from the electrical signal transmission member; and a processor configured to process and analyze the received electrical signal to directly convert it into a content of component in the saliva, the component in the saliva including glucose.

In some implementations, the terminal further includes: a display configured to display the content of component in the saliva.

According to a third aspect of the present disclosure, there is provided an operation method of the above saliva detection system, including: deforming the flexible friction power generation assembly to generate electric energy, and storing the generated electric energy by using an electrical storage element; placing the saliva detection device d in a mouth of a user, and driving the sample collector, the electrochemical sensor and the electric signal transmission component to operate by the stored electric energy to obtain detection data; transmitting the detection data to a processor for processing to obtain a detection result; and displaying the detection result through the display.

In some implementations, the deforming the flexible friction power generation assembly includes: repeatedly bending and recovering the flexible friction power generation assembly by a stepping motor or manually.

DESCRIPTION OF DRAWINGS

To more clearly illustrate technical solutions of embodiments of the present disclosure, drawings of the embodiments will be briefly introduced below, and it is apparent that the drawings in the following description only relate to some embodiments of the present disclosure and do not limit the present disclosure.

DESCRIPTION OF EMBODIMENTS

In order to make objects, technical solutions and advantages of the embodiments of the present disclosure more apparent, the technical solutions of the embodiments of the present disclosure will be described clearly and completely below with reference to the drawings of the embodiments of the present disclosure. It should be understood that the described embodiments are only a few embodiments of the present disclosure, and not all embodiments. All other embodiments, which can be derived by a person skilled in the art from the described embodiments of the present disclosure without any inventive step, are within a protection scope of the present disclosure.

Unless defined otherwise, technical or scientific terms used herein shall have an ordinary meaning as understood by ordinary skills in the art to which the present disclosure belongs. A word "comprising" or "comprises" and the like means that an element or item preceding the word includes an element or item listed after the word and its equivalent, but does not exclude other elements or items. Terms "connected" or "coupled" and the like are not restricted to a physical or mechanical connection, but may include an electrical connection, whether direct or indirect. Terms "upper", "lower", "left", "right", and the like are used only to indicate a relative positional relationship, and when an absolute position of an object being described is changed, the relative positional relationship may be changed accordingly.

Based on continuous increasing of demand for rapid and timely detection, a method and a device for detecting biomarkers in saliva with high reliability are urgently required to be developed, and in this respect, an electrochemical biological detector has excellent characteristics. When an existing electrochemical biological detector is used, an external power supply is often needed, resulting in the fact that the existing electrochemical biological detector is not convenient to be carried about and cannot perfume detection at any time and any place. In addition, a status of a saliva sample can significantly affect a detection result, for example, the saliva sample may have a small collection amount, or contain many bubbles, or may be polluted during a collection process, and an existing saliva detection device cannot well avoid such problems.

To maintain the following description of the embodiments of the present disclosure clear and concise, a detailed description of known functions and known components is omitted from the present disclosure.

Figure 1:
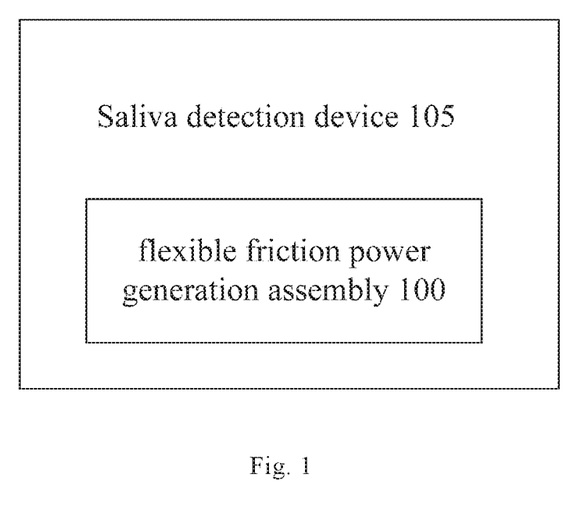
FIG. 1 is a schematic structural diagram of a saliva detection device according to an embodiment of the present disclosure.
Figure 2:
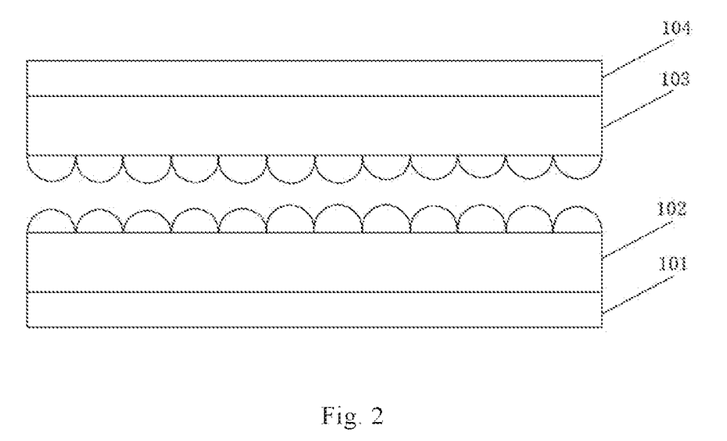
FIG. 2 is a schematic structural diagram of a flexible friction power generation assembly of a saliva detection device according to an embodiment of the present disclosure.

FIG. 1 is a schematic structural diagram of a saliva detection device according to an embodiment of the present disclosure, and as shown in FIG. 1, the present disclosure provides a saliva detection device 105, where the saliva detection device 105 includes a flexible friction power generation assembly 100 configured to supply power to the saliva detection device 105, specifically, in this embodiment, a specific structure of the flexible friction power generation assembly 100 is as shown in FIG. 2, and the flexible friction power generation assembly 100 includes: a first electrode 101; a first macromolecule polymer layer 102 which is disposed in contact with a surface of the first electrode 101 and has a concave-convex structure on a surface thereof distal to the first electrode 101; a second macromolecule polymer layer 103 having a concave-convex structure on a surface thereof proximal to the first macromolecule polymer layer 102; and a second electrode 104 disposed in contact with a surface of the second macromolecule polymer layer 103 distal to the concave-convex structure thereof, wherein when the flexible friction power generation assembly 100 is flexibly deformed, the concave-convex structures of the first macromolecule polymer layer 102 and the second macromolecule polymer layer 103 rub against each other, and an electric signal is output through the first electrode 101 and the second electrode 104. In some implementations, the flexible friction power generation assembly 100 operates as a friction power generator, and the first electrode 101 and the second electrode 104 can be used as voltage and current output electrodes of the friction power generator to provide an electric power.

In some implementations, a material of the first electrode 101 and a material of the second electrode 104 may be respectively and independently selected from conductive paste, indium tin oxide, graphene, carbon nanotube, silver nanowire film, metal or alloy, wherein the metal is gold, silver, aluminum, nickel, copper, titanium, iron or tungsten, the alloy is an aluminum alloy, an iron alloy, a magnesium alloy, a copper alloy, a zinc alloy, a lead alloy, and the like, and are not limited herein. Specifically, when layers of the flexible friction power generation assembly 100 are bent, since surfaces of the first macromolecule polymer layer 102 and the second macromolecule polymer layer 103 are both provided with concave-convex structures, the surfaces of the macromolecule polymer layers rub against each other to generate electrostatic charges, the generation of the electrostatic charges changes a capacitance between the first electrode 101 and the second electrode 104, so that a potential difference occurs between the first electrode 101 and the second electrode 104, free electrons flow from a side with a low potential to a side with a high potential through a transmission circuit (not shown in the figure) in the saliva detection device 105, and thus a current is formed in the transmission circuit, when the layers of the flexible friction power generation assembly 100 recovers to an initial state, an internal potential between the first electrode 101 and the second electrode 104 disappears, and at this time, a reverse potential difference is generated between the first electrode 101 and the second electrode 104 which had been balanced, the free electrons form a reverse current through the transmission circuit. As such, in some implementations, the flexible friction power generation assembly 100 is configured to output a periodic alternating current signal through the first electrode 101 and the second electrode 104 by repeatedly bending and recovering. Thus, by repeatedly rubbing and recovering of the flexible friction power generation assembly 100, the periodic alternating current signal can be formed in the transmission circuit to supply power to the saliva detection device 105.

Figure 3:
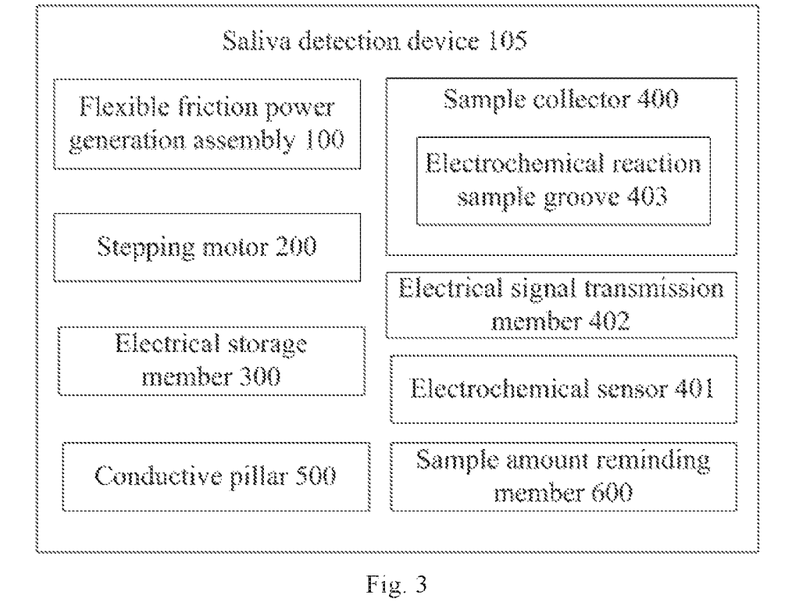
FIG. 3 is a schematic structural diagram of a saliva detection device according to an embodiment of the present disclosure.

In some implementations, the flexible friction power generation assembly 100 can be repeatedly bent and recovered, either manually or by a motor, to cause the first electrode 101 and the second electrodes 104 to output the periodic alternating current signal. In some implementations, as shown in FIG. 3, the saliva detection device 105 may further include: a stepping motor 200 configured to periodically oscillate to drive the flexible friction power generation assembly 100 to be repeatedly bent and recovered. Specifically, the stepping motor 200 may be an open-loop control element capable of converting an electric pulse signal into an angular displacement or a linear displacement, and a speed and an acceleration of rotation of the stepping motor 200 can be controlled by controlling a pulse frequency, so that the stepping motor periodically oscillates to drive the flexible friction power generation assembly 100 to be repeatedly bent and recovered, and thus the periodic alternating current signal is generated. As an example of the present disclosure, the stepping motor 200 for periodically driving the flexible friction power generation assembly 100 may have an oscillation frequency of 0.33 Hz to achieve an approximately 0.3% deformation, which causes the maximum output voltage of the flexible friction power generation assembly 100 to reach 8V and the maximum output current of the flexible friction power generation assembly 100 to reach 9 µA.

In some implementations, as shown in FIG. 3, the saliva detection device 105 may further have an electrical storage member 300 configured to store electrical energy generated by the flexible friction power generation assembly 100. In some implementations, the electrical storage element 300 may be an energy storage capacitor, a storage battery, or the like, and may be directly coupled to the first electrode 101 and the second electrode 104 to store electric energy generated by the flexible friction power generation assembly 100, or may be coupled to the transmission circuit in the saliva detection device 105 to supply power to the saliva detection device 105 by using remaining electric power therein, so that a user does not need to make the flexible friction power generation assembly 100 generate electric power each time before using the saliva detection device 105, and only when the electric power in the electrical storage element 300 is insufficient, the flexible friction power generation assembly 100 deforms to generate electric power, which is convenient and fast to use, and capable of significantly increasing a service life of the flexible friction power generation assembly 100.

In some implementations, each of the concave-convex structures of the first macromolecule polymer layer 102 and the second macromolecule polymer layer 103 facing each other is a concave-convex structure of micro and/or nano level, and the first macromolecule polymer layer 102 and the second macromolecule polymer layer 103 having the concave-convex structures may be prepared through various processes. For example, a macromolecule polymer colloidal solution may be coated on a surface of a template subject to a roughening treatment, and then dried by a drying operation and peeled off; alternatively, the macromolecule polymer colloidal solution may be coated on a flat surface of the template, and then dried by a drying operation and peeled off to obtain a flat macromolecule polymer layer, and a surface of the flat macromolecule polymer layer is subjected to a roughening treatment, for example, by sanding with a sand paper, to obtain the macromolecule polymer layer having the uneven structure.

In some implementations, the template may be a metal plate, a glass substrate, a silicon substrate, or the like. In some implementations, the macromolecule polymer may be any one or more of polydimethylsiloxane (PDMS), polymethyl methacrylate (PMMA), polyvinyl acetate (PVA), polyacrylamide (PAN), polyvinylidene fluoride (PVDF), a polyimide film, a polyoxymethylene film, an ethyl cellulose film, a polyamide film, a polyethylene glycol succinate film, a cellulose acetate film, a fiber (regenerated) sponge film, a rayon film, a polymethyl methacrylate film, and the like, which is not particularly limited herein. In some implementations, the drying operation may be performed at a room temperature for 10 hours, or may be performed with heating to a degree ranging from 45 degrees Celsius to 75 degrees Celsius for a time ranging from 4 hours to 6 hours.

In some implementations, there is a difference in friction electrode sequence between the material of the first macromolecule polymer layer 102 and the material of the second macromolecule polymer layer 103. For example, the material of the first macromolecule polymer layer 102 and the material of the second macromolecule polymer layer 103 may be different from each other. The "friction electrode sequence" described in the present disclosure is a sequence of the material of the macromolecule polymer layer according to its attraction degree to charges, and at the moment when materials of two macromolecule polymer layers contact and rub against each other, negative charges at rubbing surfaces are transferred from a surface of the material with the friction electrode sequence being a positive polarity to a surface of the material with the friction electrode sequence being a negative polarity, and it is generally believed that transferring of charges is related to a surface work function of the material of the macromolecule polymer layer, which is realized by transferring of electrons or ions at the rubbing surfaces. It should be noted that the friction electrode sequence is only a statistical result based on experiences, that is, the farther the difference in friction electrode sequence between the materials of the two macromolecule polymer layers is, the greater the probability that charges generated after their contact have a positive or negative polarity consistent with the friction electrode sequence, and an actual result is influenced by many factors, such as the surface roughness of the materials, ambient humidity, and whether there is a relative friction. By making a difference in friction electrode sequence between the material of the first macromolecule polymer layer 102 and the material of the second macromolecule polymer layer 103 exist, transferring of charges and accordingly power generation in the flexible friction power generation assembly 100 can be facilitated.

Figure 4A:
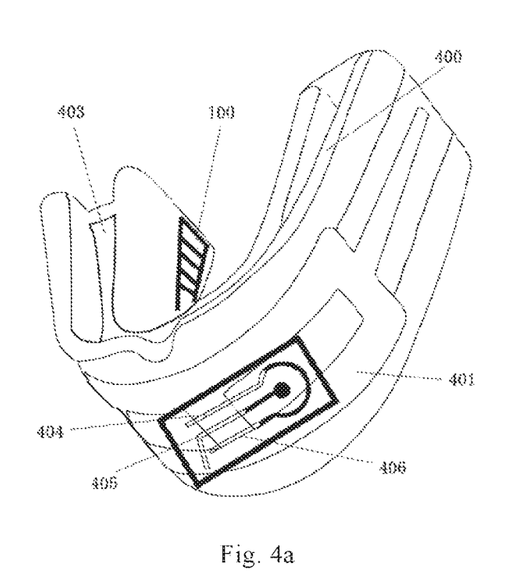
FIG. 4*a* is a schematic structural diagram of a saliva detection device according to an embodiment of the present disclosure.
Figure 4B:
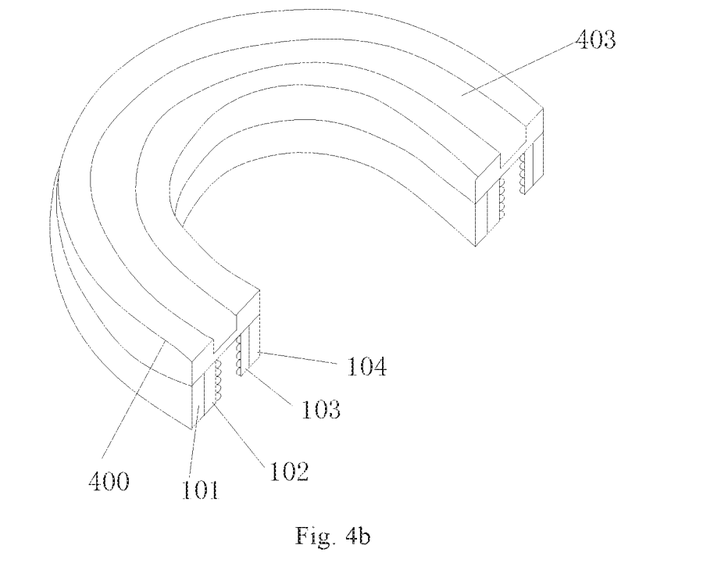
FIG. 4*b* is a schematic structural diagram of a saliva detection device according to an embodiment of the present disclosure.

In some implementations, as shown in FIG. 3, the saliva detection device 105 further includes a sample collector 400, an electrochemical sensor 401, and an electrical signal transmission member 402. For example, as shown in FIG. 4, the sample collector 400 has a curvature such that a middle part thereof is lower than two ends thereof, and is provided with an electrochemical reaction sample groove 403 therein, the sample collector 400 with such a structure is more easily attached to teeth, so that the collected saliva sample is gathered to the middle part of the sample collector 400, so as to rapidly collect the saliva sample; the electrochemical sensor 401 is arranged in the electrochemical reaction sample groove 403 to detect components in the saliva sample and generate corresponding electric signals; and the electrical signal transmission member 402 (not shown in FIGS. 4a and 4b) is configured to transmit an electrical signal collected by the electrochemical sensor 401 to a microcontroller in the saliva detection device or an external electronic device or server for further analyzing the components in the saliva sample, which is not particularly limited herein. In some implementations, the sample collector 400 is made of a flexible material, for example, a flexible macromolecule polymer used for preparing the first macromolecule polymer layer and the second macromolecule polymer layer as described above, such as any one or more of polydimethylsiloxane (PDMS), polymethyl methacrylate (PMMA), polyvinyl acetate (PVA), polyacrylamide (PAN), polyvinylidene fluoride (PVDF), polyimide film, polyoxymethylene film, ethyl cellulose film, polyamide film, polyethylene glycol succinate film, cellulose acetate film, fiber (regenerated) sponge film, artificial fiber film, polymethyl methacrylate film, etc., which is not limited in particular.

In some implementations, as shown in FIG. 4a, the flexible friction power generation assembly 100 may be disposed at a bottom of the sample collector 400 and wrapped with a flexible waterproof insulating material. Specifically, in this embodiment, the first electrode, the first macromolecule polymer layer, the second macromolecule polymer layer and the second electrode of the flexible friction power generation assembly are stacked in a stacking direction perpendicular to an opening direction of the electrochemical reaction sample groove. The flexible friction power generation assembly 100 has a dimension corresponding to that of a cross section of the sample collector 400 taken along the stacking direction, i.e., a thickness of about 380 µm. With such configuration, the flexible friction power generation assembly 100 can be bent and recovered along the curvature of the sample collector. The flexible friction power generation assembly 100 may be adhered to the bottom of the sample collector 400 by using conductive adhesive, and the flexible friction power generation assembly 100 is wrapped by the flexible waterproof insulating material, so that the flexible friction power generation assembly 100 is prevented from being wetted by the saliva or leaking the generated electric energy, the service life of the flexible friction power generation assembly is prolonged, and a use safety of the saliva detection device 105 is improved.

FIG. 4b shows a schematic diagram of a composite member of the flexible friction power generation assembly 100 and the sample collector 400. As can be seen from the above description, each of the flexible friction power generation assembly 100 and the sample collector 400 is made of a flexible material and thus both of them can have a similar curvature, and by bending and recovering the composite member, the concave-convex structures of the first macromolecule polymer layer 102 and the second macromolecule polymer layer 103 in the flexible friction power generation assembly are rubbed against each other to generate electric energy. FIG. 4b is merely illustrative of a way of arranging the flexible friction power generation assembly 100 and the sample collector 400. The present disclosure is not limited to this, and the flexible friction power generation assembly 100 is further externally provided with a flexible insulating material package. A width of the flexible friction power generation assembly 100 may be the same as that of the sample collector 400, so as to be conveniently disposed in an oral cavity for collecting and detecting the saliva.

In some implementations, each of the first macromolecule polymer layer 102 and the second macromolecule polymer layer 103 is made of a hydrophobic material. Specifically, the hydrophobic material (e.g., hydrophobic paper) being used for the first macromolecule polymer layer 102 and the second macromolecule polymer layer 103 can reduce a sensitivity of the flexible friction power generation assembly 100 to humidity of environment, even if the flexible friction power generation assembly 100 is in contact with the saliva sample, the flexible friction power generation assembly will not be wetted, and an efficiency of power generation thereof will not be affected, moreover, a printing resolution of a metal electrode can be improved by minimizing a tailing effect of spraying a material (such as nickel ink) of the metal electrode, and in addition, the hydrophobic material can prevent the material of the first electrode 101 and the second electrode 104 from diffusing into the macromolecule polymer layer.

The saliva has a variety of components, significant for diagnosis, to be detected, such as glucose, salivary amylase, lysozyme, viral antibodies, and the like. Taking the electrochemical sensor 401 configured to detect a content of glucose in the saliva as an example, as shown in FIG. 4, the electrochemical sensor 401 may include a reference electrode 404 for providing a reference potential and keeping the potential stable, a working electrode 405, and a counter electrode 406 for providing a return circuit. In some implementations, the working electrode 405 is in a form of nanospheres which are loaded with riboflavin adenine nucleotide complex glucose dehydrogenase or glucose oxidase. The working electrode 405 in the form of nanospheres has a small volume, so that the working electrode 405 can be conveniently integrated on the electrochemical sensor 401, the riboflavin adenine nucleotide complex glucose dehydrogenase or the glucose oxidase on the working electrode 405 can act with the glucose in the saliva to generate an electric signal, the electrochemical sensor 401 can collect the electric signal by adopting a coulometric method, that is, all generated electric signals are involved in calculation, and thus a lower content of glucose in the saliva sample can be accurately detected. In the embodiment, a thin-film gold electrode is used as the working electrode 405 of the electrochemical sensor 401, an Ag/AgCl electrode is used as the reference electrode 404 of the electrochemical sensor 401, a gold electrode is used as the counter electrode 406 of the electrochemical sensor 401, an organic functional material is used as an electron mediator, and glutaraldehyde is used for crosslinking and fixing the glucose oxidase.

The electrochemical sensor 401 may be manufactured using various processes. For example, taking the thin-film gold electrode as the working electrode 405, the Ag/AgCl electrode as the reference electrode 404, and the gold electrode as the counter electrode 406 as an example, a manufacturing process of the electrochemical sensor 401 may include: drawing a strip-shaped mask pattern on a plastic substrate with a protective film; sputtering a nickel-chromium/gold (10 nm/100 nm) electrode layer on the plastic substrate in vacuum by a micro-electro-mechanical system (MEMS) process; removing the mask to obtain a gold electrode array, wherein a thickness of the gold layer is less than 100 nm; silk-screen printing Ag/AgCl mixed slurry on the reference electrode by adopting a silk-screen printing process, and drying in a drying oven at 120° C. for 5 minutes to prepare an Ag/AgCl reference electrode; and sticking a double-sided adhesive tape on the plastic substrate to expose the basic working electrode, the Ag/AgCl reference electrode and the gold counter electrode. Specifically, an electrocatalytic oxidation of glucose is a kinetic control process, and therefore, a modification needs to be performed on the basic working electrode of the electrochemical sensor 401 to form a catalytic material film with a high specific surface area on a surface of the basic working electrode, and a response signal of a kinetically controlled electrochemical process can be improved by screening the catalytic material, so as to reduce a detection limit of glucose. Specifically, before modifying the basic working electrode obtained in the manufacturing process of the electrochemical sensor 401, first, the basic working electrode needs to be placed in an ultrasonic cleaner, to be cleaned with deionized water for 5 minutes, and to be taken out and naturally dried, then 5 μL ferrocene ethanol solution with a concentration 0.1 mol/L of ferrocene ethanol is dripped on a surface of the prepared basic working electrode, and after being dried at the room temperature, the basic working electrode is modified, and a specific modification process for modifying the basic working electrode includes the following steps: taking 1.5 U/μL glucose oxidase (GOD) solution with a concentration 1.5 U/μL of glucose oxidase and dripping the GOD solution on the surface of the basic working electrode which is preliminarily modified by the ferrocene ethanol solution; dripping 1 μL bovine serum albumin (BSA) with a mass fraction of 1%, and then drying the basic working electrode at the room temperature; dripping 1.5 μL glutaraldehyde solution with a mass fraction of 1.5% to perform enzyme crosslinking and fixation; washing away free enzyme and monomer, which are not fixed, by deionized water, naturally drying at the room temperature to form a film to obtain the working electrode 405, and storing the working electrode 405 in a refrigerator with a temperature of 4° C. for later use. The electrochemical sensor 401 manufactured in this embodiment has good stability and excellent performance, and can detect a low content of glucose in the saliva. In some implementations, as shown in FIG. 3, the saliva detection device 105 further includes: a conductive pillar 500 arranged on the sample collector 400 and used for electrically stimulating a salivary gland of an examinee wearing the saliva detection device 105. Specifically, the conductive pillar 500 receives a control command sent by the microcontroller in the saliva detection device 105 or the external electronic device or server, and electrically stimulates the salivary gland of the examinee wearing the saliva detection device 105 according to preset parameters, so as to reduce a collection time of the saliva sample.

In some implementations, an outer wall of the sample collector 400 is provided with a liquid inlet for allowing the saliva entering the electrochemical reaction sample groove 403, and the liquid inlet can make the saliva quickly enter the electrochemical reaction sample groove 403, and simultaneously prevent the saliva from contacting with other components in the saliva detection device 105, so as to avoid affecting a performance of the saliva detection device 105.

In some implementations, as shown in FIG. 3, the saliva detection device 105 further includes: a sample amount reminding member 600 configured to determine an amount of the saliva sample in the electrochemical reaction sample groove 403, and to issue a reminder and initiate a detection of the electrochemical sensor 401 in response to that the detected amount of the saliva sample reaches a preset threshold. In some implementations, the sample amount reminding member 600 may determine the amount of the saliva sample according to various parameters such as humidity, liquid level, pressure, etc. in the electrochemical reaction sample groove 403, and correspondingly, sensors for acquiring the parameters are disposed in the electrochemical reaction sample groove 403.

In some implementations, the sample amount reminding member 600 comprises any one of the following means provided in the electrochemical reaction sample groove 403 to determine the amount of the saliva sample in the electrochemical reaction sample groove 403 based on the detection result of the means: a humidity sensor configured to detect humidity within the electrochemical reaction sample groove; a liquid level sensor configured to detect a liquid level inside the electrochemical reaction sample groove 403; and a pressure sensor configured to detect a pressure in the electrochemical reaction sample groove 403, wherein the sample reminding member 600 determines the amount of the saliva sample according to the detection result of the means disposed in the electrochemical reaction sample groove 403, so that a proper amount of the saliva sample can be obtained, the detection result is prevented from being affected by insufficient amount of the saliva sample, and a reminder can be timely sent to a user when the proper amount of the saliva sample is obtained, so that the operation is convenient and fast.

In some implementations, the saliva detection device 105 may further include a microcontroller and a display, the microcontroller receives the electrical signal collected by the sensor and processes and analyzes the electrical signal to obtain a content of component in the saliva, and the display is used for displaying a result of processing and analyzing, so as to realize the intelligent and portable saliva detection device 105. In some implementations, the saliva detection device 105 may further include a wireless transceiver element for transmitting the electrical signal to the external electronic device or server, such as a mobile phone, a computer, a cloud, and an energy storage element for storing the electrical energy generated by the flexible friction power generation assembly 100. The saliva detection device 105 provided by the present disclosure utilizes the flexible friction power generation assembly 100 to supply power to the saliva detection device 105, realizes an integration of power supply, sampling and detection, and is efficient and convenient.

In some implementations, only detection and electrical signal transmission functions may be retained in the saliva detection device 105, and the processing of the electrical signal related to the component in the saliva may be implemented by a terminal, so that the structure of the saliva detection device 105 worn in the oral cavity can be more compact, and a user friendliness is improved; further, a plurality of saliva detection devices 105 may be communicatively coupled to a same terminal to perform a saliva component analysis and display by the same terminal, so that the plurality of saliva detection devices 105 can share the same terminal, thereby reducing a cost of a saliva detection system and facilitating maintenance work when a certain device fails.

Figure 5:
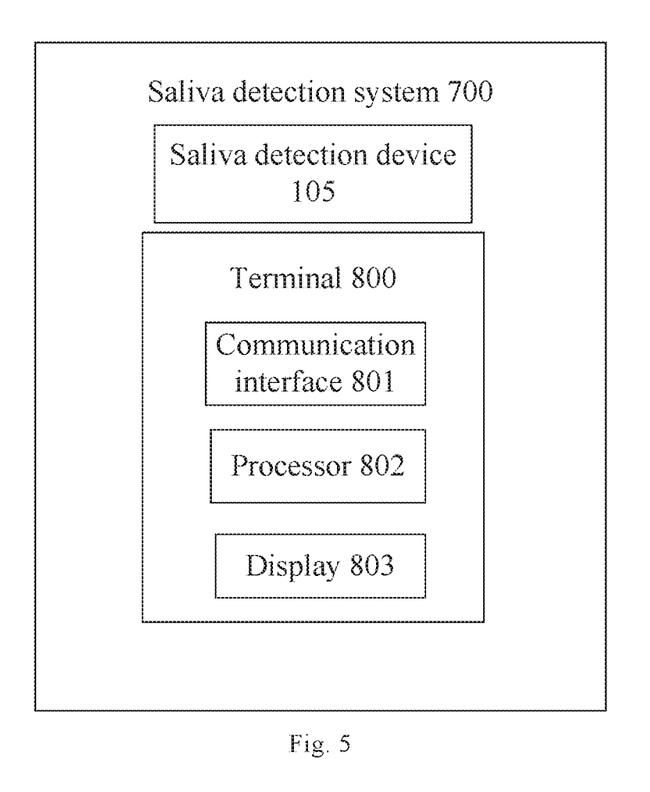
FIG. 5 is a schematic structural diagram of a saliva detection system according to an embodiment of the present disclosure.

FIG. 5 is a schematic structural diagram of a saliva detection system according to an embodiment of the present disclosure, and as shown in FIG. 5, the embodiment of the present disclosure further provides a saliva detection system 700 including the saliva detection device 105 according to the embodiment of the present disclosure and a terminal 800, where the terminal 800 includes: a communication interface 801 configured to receive an electrical signal transmitted from the electrical signal transmission member 402; and a processor 802 configured to process and analyze the received electrical signal to directly convert them into a content of component in the saliva, the component in the saliva including glucose. In some implementations, the terminal 800 may include a mobile phone, a tablet computer, a server, etc., the electrical signal transmission member 402 may be a transmission wire, specifically, the transmission wire is coupled to the communication interface 801 of the terminal and a communication interface of the saliva detection device 105, so as to transmit the electrical signal collected by the electrochemical sensor 401 to the processor 802 in the terminal 800, the processor 802 may set a data processing process of the electrical signal as a direct reading form, that is, a form of a standard curve, a standard table, etc., the content of component in the saliva is directly read according to the electrical signal, and repeated data processing is not required, which can greatly accelerate the data processing process, and power consumption can be reduced. The saliva detection system 700 provided by the present disclosure supplies power to the saliva detection device 105 by using the flexible friction power generation assembly 100, realizes an integration of power supply, sampling and detection, and is efficient and convenient.

In some implementations, the terminal 800 may further include: a display 803 configured to display the content of component in the saliva. In some implementations, the display 803 may display the content of component in the saliva in various forms such as a curve, a table, etc., so that the user can quickly read the content of component in the saliva.

Figure 6:
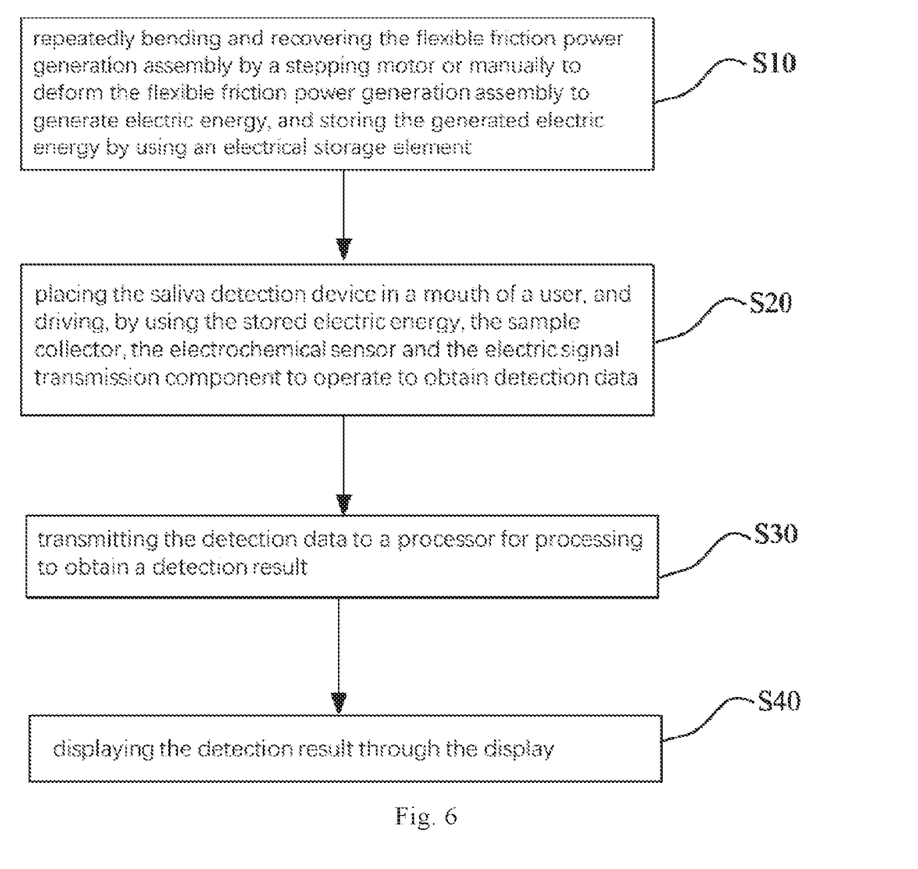
FIG. 6 is a flow chart of an operation method of a saliva detection system according to an embodiment of the present disclosure.

An embodiment of the present disclosure further provides an operation method of the saliva detection system, including: step S10, repeatedly bending and recovering the flexible friction power generation assembly by a stepping motor or manually to deform the flexible friction power generation assembly to generate electric energy, and storing the generated electric energy by using an electrical storage element; step S20, placing the saliva detection device in a mouth of a user, and driving, by using the stored electric energy, the sample collector, the electrochemical sensor and the electric signal transmission component to operate to obtain detection data; step S30, transmitting the detection data to a processor for processing to obtain a detection result; and step S40, displaying the detection result through the display.

The above description is intended to be illustrative, and not restrictive. For example, the above-described examples (or one or more versions thereof) may be used in combination with each other. For example, other embodiments may be utilized by those of ordinary skill in the art upon reading the foregoing description. In addition, in the foregoing detailed description, various features may be grouped together to streamline the present disclosure, which should not be interpreted as an intention that a non-claimed disclosed feature is essential to any claim. Rather, the subject matter of the present disclosure may lie in less than all features of a particular disclosed embodiment. Thus, claims are hereby incorporated into the detailed description as examples or embodiments, with each claim standing on its own as a separate embodiment, and it is contemplated that the embodiments may be combined with each other in various combinations or permutations. The scope of the present disclosure should be determined with reference to the appended claims, along with the full scope of equivalents to which such claims are entitled.

The above embodiments are only exemplary embodiments of the present disclosure, and are not intended to limit the present disclosure, the scope of which is defined by the claims. Various modifications and equivalents of the present disclosure herein disclosed may occur to persons skilled in the art and are intended to be included within the spirit and scope of the present disclosure.

The invention claimed is:

1. A saliva detection device, comprising a flexible friction power generation assembly configured to supply power to the saliva detection device and, in turn, comprising:
   a first electrode;
   a first macromolecule polymer layer which is disposed in contact with a surface of the first electrode and has a concave-convex structure on a surface thereof distal to the first electrode;
   a second macromolecule polymer layer having a concave-convex structure on a surface thereof proximal to the first macromolecule polymer layer; and
   a second electrode disposed in contact with a surface of the second macromolecule polymer layer distal to the concave-convex structure thereof, wherein in response to deformation of the flexible friction power generation assembly, the concave-convex structures of the first macromolecule polymer layer and the second macromolecule polymer layer rub against each other, and an electric signal is output through the first electrode and the second electrode, the saliva detection device further comprises a sample collector, an electrochemical sensor, and an electrical signal transmission member, wherein the sample collector has a curvature such that a middle part thereof is lower than two ends thereof, and an electrochemical reaction sample groove is arranged in the sample collector;

the electrochemical sensor is arranged in the electrochemical reaction sample groove to detect component in a saliva sample and generate a corresponding electric signal; and the electrical signal transmission member is configured to smit the electrical signal;

wherein the flexible friction power generation assembly is disposed at a bottom of the sample collector and is wrapped by a flexible waterproof insulating material;

wherein the first electrode, the first macromolecule polymer layer, the second macromolecule polymer layer and the second electrode of the flexible friction power generation assembly are stacked in a stacking direction perpendicular to an opening direction of the electrochemical reaction sample groove, and a thickness of the flexible friction power generation assembly is approximately equal to a dimension of a cross section of the sample collector taken along the stacking direction; and wherein the thickness of the friction power generation assembly is about 380 μm.

2. The saliva detection device of claim 1, wherein the deformation of the flexible friction power generation assembly includes bending, and the flexible friction power generation assembly is configured to output a periodic alternating current signal through the first electrode and the second electrode by repeatedly bending and recovering.

3. The saliva detection device of claim 2, further comprising: a stepping motor configured to periodically oscillate to drive the flexible friction power generation assembly to repeatedly bend and recover.

4. The saliva detection device of claim 1, further comprising: an electrical storage element configured to store electrical energy generated by the flexible friction power generation assembly.

5. The saliva detection device of claim 1, wherein each of the concave-convex structures is a micro-scale and/or nano-scale concave-convex structure.

6. The saliva detection device of claim 1, wherein there is a difference between a material of the first macromolecule polymer layer and a material of the second macromolecule polymer layer, and/or a difference between surface roughness of a material of the first macromolecule polymer layer and a material of the second macromolecule polymer layer.

7. The saliva detection device of claim 1, wherein
the sample collector has an overall curvature such that both ends thereof are higher than the middle part in a length direction thereof, and
the electrochemical reaction sample groove is arranged in the sample collector for collecting the saliva sample.

8. The saliva detection device of claim 7, wherein,
the sample collector is made of a flexible material the same as that of the first macromolecule polymer layer and the second macromolecule polymer layer.

9. The saliva detection device of claim 1, wherein the first macromolecule polymer layer and the second macromolecule polymer layer are made of a hydrophobic material.

10. The saliva detection device of claim 1, further comprising:
a conductive pillar arranged on the sample collector and configured to electrically stimulate a salivary gland of an examinee wearing the saliva detection device.

11. The saliva detection device of claim 1, wherein the sample collector has a liquid inlet on an outer wall thereof for allowing the saliva sample to enter the electrochemical reaction sample groove.

12. The saliva detection device of claim 1, further comprising:
a sample amount reminding member configured to determine an amount of the saliva sample in the electrochemical reaction sample groove, and to issue a reminder and initiate a detection of the electrochemical sensor in response to the detected amount of the saliva sample reaching a preset threshold.

13. The saliva detection device of claim 12, wherein the sample amount reminding member comprises any one of the following means disposed in the electrochemical reaction sample groove to determine the amount of the saliva sample in the electrochemical reaction sample groove based on a detection result of the means:
a humidity sensor configured to detect humidity within the electrochemical reaction sample groove;
a liquid level sensor configured to detect a liquid level within the electrochemical reaction sample groove; and
a pressure sensor configured to detect a pressure within the electrochemical reaction sample groove.

14. The saliva detection device of claim 1, wherein the electrochemical sensor is configured to detect a content of glucose in the saliva sample and comprises a working electrode in a form of nanospheres which are loaded with riboflavin adenine nucleotide complex glucose dehydrogenase or glucose oxidase.

15. A saliva detection system comprising the saliva detection device of claim 1 and a terminal, the terminal comprising:
a communication interface configured to receive the electrical signal transmitted from the electrical signal transmission member; and
a processor configured to process and analyze the received electrical signal to directly convert it into a content of a component in the saliva sample, the component in the saliva sample comprising glucose, wherein the terminal further comprises:
a display configured to display the content of the component in the saliva sample.

16. An operation method of the saliva detection system as claimed in claim 15, comprising:
deforming the flexible friction power generation assembly to generate electric energy, and storing the generated electric energy by using an electrical storage element;
placing the saliva detection device in a mouth of a user, and driving the sample collector, the electrochemical sensor and the electric signal transmission component to operate by using the stored electric energy to obtain detection data;
transmitting the detection data to a processor for processing to obtain a detection result; and
displaying the detection result through the display, wherein,
the deforming the flexible friction power generation assembly comprises: repeatedly bending and recovering the flexible friction power generation assembly by a stepping motor or manually.

\* \* \* \* \*